US011439985B2

(12) United States Patent
Umbarkar et al.

(10) Patent No.: US 11,439,985 B2
(45) Date of Patent: Sep. 13, 2022

(54) NITRATION OF BENZENE

(71) Applicant: Council of Scientific & Industrial Research, New Delhi (IN)

(72) Inventors: Shubhangi Bhalchandra Umbarkar, Pune (IN); Atul Balasaheb Kulal, Pune (IN); Mohan Keraba Dongare, Pune (IN)

(73) Assignee: Council of Scientific & Industrial Research

( * ) Notice: Subject to any disclaimer, the term of this patent is extended or adjusted under 35 U.S.C. 154(b) by 117 days.

(21) Appl. No.: 16/769,959

(22) PCT Filed: Dec. 5, 2018

(86) PCT No.: PCT/IN2018/050815
§ 371 (c)(1),
(2) Date: Jun. 4, 2020

(87) PCT Pub. No.: WO2019/111280
PCT Pub. Date: Jun. 13, 2019

(65) Prior Publication Data
US 2020/0384445 A1    Dec. 10, 2020

(30) Foreign Application Priority Data
Dec. 7, 2017 (IN) .............................. 201711043853

(51) Int. Cl.
*B01J 23/30* (2006.01)
*B01J 37/02* (2006.01)
*C07C 201/08* (2006.01)
*C07C 205/06* (2006.01)

(52) U.S. Cl.
CPC ............ *B01J 23/30* (2013.01); *B01J 37/0236* (2013.01); *C07C 201/08* (2013.01); *C07C 205/06* (2013.01)

(58) Field of Classification Search
CPC ..... B01J 23/30; B01J 37/0236; C07C 201/08; C07C 205/06
See application file for complete search history.

(56) References Cited

U.S. PATENT DOCUMENTS

2003/0193037 A1* 10/2003 Koyanagi .............. B82Y 30/00
252/1

FOREIGN PATENT DOCUMENTS

| CN | 101050181 A | 10/2007 |
| WO | 2008075901 A1 | 6/2008 |
| WO | 2014195973 A2 | 12/2014 |

OTHER PUBLICATIONS

International Search Report for PCT/IN2018/050815 dated Feb. 26, 2019; 2 pages.
Kulal AB, Dongare MK, Umbarkar SB. Sol-gel synthesised WO3 nanoparticles supported on mesoporous silica for liquid phase nitration of aromatics. Applied Catalysis B: Environmental. Mar. 1, 2016;182:142-52.

(Continued)

*Primary Examiner* — Brian A McCaig
(74) *Attorney, Agent, or Firm* — Lerner, David, Littenberg, Krumholz & Mentlik, LLP

(57) ABSTRACT

The present invention discloses a process for nitration of benzene. More particularly, the present invention discloses an efficient, environmental friendly process for the nitration of benzene using a modified solid acid catalyst.

12 Claims, 5 Drawing Sheets

(56) References Cited

OTHER PUBLICATIONS

Shi L, Kai W, Yang CF, Qian H, Liu DB, Pan RM. Synthesis, characterization of Nafion-functionalized MCM-41 and its catalytic application in preparation of CL-20 via HNO3 electrolyte involved nitration of TAIW. Journal of Saudi Chemical Society. Jul. 1, 2018;22(5):588-93.

* cited by examiner

NITRATION OF BENZENE

CROSS-REFERENCE TO RELATED APPLICATIONS

This application is a national phase entry under 35 U.S.C. § 371 of International Application No. : PCT/IN2018/050815, filed Dec. 5, 2018, which claims priority to India Patent Application No.: 201711043853, filed Dec. 7, 2017.

FIELD OF THE INVENTION

The present invention relates to a process for nitration of benzene. More particularly, the present invention relates to an efficient, environmental friendly process for the nitration of benzene using a modified solid acid catalyst.

BACKGROUND AND PRIOR ART OF THE INVENTION

Aromatic nitro compounds are an important class of compounds used in industry for the manufacture of dyes, pharmaceuticals and fine chemicals. These are conventionally manufactured by using nitrating mixture (concentrated sulphuric acid and fuming nitric acid) as nitrating agent and large quantity of dilute sulphuric acid is generated as waste. This dilute sulphuric acid needs to be concentrated for its reuse which is highly energy intensive process or has to be disposed which poses environmental problems. Thus aromatic nitration is one of the most hazardous industrial processes. Apart from the environmental hazards, the selectivity for the desired product is also low in the conventional process. Hence, nitration of aromatics using solid acid catalyst without use of sulphuric acid is highly desired to overcome the above mentioned problems. Various solid catalysts have been tried either for liquid phase or vapor phase nitration of aromatics with limited success because of lower conversions or deactivation of the solid acid catalyst.

In a prior patent application WO2014195973, the inventors have used sol gel synthesized $WO_3/SiO_2$ catalyst for liquid phase nitration of aromatics. $WO_3/SiO_2$ catalyst showed highly hydrophilic nature due to surface silanol groups. But this had an adverse effect on catalytic activity. An additional solvent viz ethylene dichloride was needed to remove the water from the reaction to prevent catalyst deactivation.

Article titled "Sol gel synthesised $WO_3$ nanoparticles supported on mesoporous silica for liquid phase nitration of aromatics" by Kulal, A B et al. published in Applied Catalysis B: Environmental; 2016, 182; pp 142-152 reports A series of $WO_3/SiO_2$ catalysts have been prepared by sol-gel method using ammonium metatungstate and ethyl silicate-40 (ES-40) as WO3 and SiO2 precursors respectively. The sol-gel method has led to the formation of $WO_3$ nanoparticles of 2-5 nm well dispersed on mesoporous silica along with some $WO_3$' agglomerates. Formation of monoclinic $WO_3$ was seen on the catalysts above 5 wt % $WO_3$ loading by XRD analysis. Silica has shown very high surface area of 606 $m^2/g$ which decreased gradually upto 368 $m^2/g$ with 20 wt % $WO_3$ loading. 20 wt % $WO_3/SiO_2$ catalyst has shown maximum acidity (0.56 mmol $NH_3/g$) with presence of both Lewis and Bronsted acidity. UV-vis DRS analysis showed formation of polytungstate species along with $WO_3$ on silica surface. The prepared catalysts were used for liquid phase nitration of aromatics using 70% nitric acid as nitrating agent without using any sulfuric acid. Very high conversion (99%) was obtained for p-cresol nitration with very high selectivity (99%) for 2-nitro p-cresol. The water formed during the reaction was removed azeotropically using ethylene dichloride as solvent. In case of o-xylene 74% conversion was obtained with 54% selectivity for 4-nitro o-xylene. The effect of different $WO_3$ precursors on nitration efficiency was studied using sodium tungstate and tungstic acid as precursors. However, ammonium metatungstate showed the highest acidity. Sodium tungstate showed formation of dimer of sodium tungstate which did not show any acidity and hence no activity for nitration. The mechanism for nitration using $WO_3/SiO_2$ has been proposed based on polarisation of water on tungsten centre generating Bronsted acidity which can further generate nitronium ion giving subsequently nitration of the aromatic ring.

Article titled "Synthesis, characterization of Nafion-functionalized MCM-41 and its catalytic application in preparation of CL-20 via $HNO_3$ electrolyte involved nitration of TAIW" by L Shi et al. published in Journal of Saudi Chemical Society, 2018, 22 (5), pp 588-593 (Available online 28 Oct. 2017) reports hybrid organic-inorganic MCM-41 (Mobil Composition of Matter No. 41) silica functionalized with Nafion (perfluoroalkylsulfonic acid analogous) prepared and characterized by Fourier Transform infrared spectroscopy (FTIR), X-ray diffraction (XRD), and $N_2$ adsorption analysis. The prepared catalyst (SA/MCM-41) exhibited high catalytic activity in the nitration of TAIW (tetraacetylhexaazaisowurtzitan) aiming at synthesizing CL-20 (hexanitrohexaazaisowurtzitane), with the yield up to 93%. The leaching problem was not observed after several runs, demonstrating that the catalyst could be recycled and reused without losing activity.

The prior art processes produces large quantity of dilute sulphuric acid as hazardous waste. Since the acids used are concentrated, the material of construction for the plant is quite costly increasing the overall basic investment. The safety aspects involved in handling these concentrated acids in large qualities needs to be implemented while operating such plants. The solid acids tried before are not very active for the nitration of aromatics and hence lower conversions are obtained as well as the catalysts get deactivated during the nitration reaction.

Therefore, to avoid prior art drawbacks there is need for an environmentally benign process for nitration of benzene. Accordingly, the present invention provides a simple, cost effective and environmentally benign process for nitration of benzene.

OBJECTIVES OF THE INVENTION

The main objective of the present invention is to provide a process for the nitration of benzene with high selectivity for mono nitrated benzene.

Another objective of the present invention is to provide a grafted hydrophobic solid acid catalyst that does not get deactivated during the nitration of benzene.

SUMMARY OF THE INVENTION

Accordingly the present invention provides a grafted hydrophobic solid acid $WO_3/SiO_2$ catalyst for nitration of benzene.

In an embodiment the catalyst is post grafted with organosilane selected from C2 to C10 alkyl trialkoxysilane where alkoxy is methoxy, ethoxy or propoxy.

The present invention also provides a process for preparing grafted hydrophobic solid acid catalyst comprising the steps of:
a) dispersing 20% $WO_3/SiO_2$ catalyst is dry toluene:
b) adding organosilane selected from alkyl trialkoxysilane to the reaction mixture of step a;
c) heating the resultant mixture with constant mixing to obtain powder from and
d) drying the resultant powder oven to obtain grafted hydrophobic solid acid catalyst.

In an embodiment the ratio of $WO_3/SiO_2$ to dry toluene is 1:4 to 1:20.

The present invention also provides a process for nitration of benzene and grafted hydrophobic solid acid catalyst for use in nitration of benzene.

In an embodiment, the present invention provides a process for the nitration of benzene with high selectivity for mono nitrated benzene using grafted hydrophobic solid acid catalyst comprising the steps of:
a) charging benzene and a grafted hydrophobic solid acid catalyst in the range of 1:0.1 to 1:1 in a reactor flushed with nitrogen followed by refluxing the reaction mixture at temperature in the range of 90 to 110° C. for the period in the range of 1 to 2 hour and
b) adding nitric acid to the reaction mixture of step (a) with constantly removing the water formed by azeotropic distillation followed by refluxing the reaction mixture at temperature in the range of 90 to 110° C. for the period in the range of 6 to 8 hour to afford mononitrobenzene.

In a preferred embodiment, the solid acid catalyst is, $WO_3/SiO_2$ catalyst which is post grafted with commercial organosilanes.

The conversion of benzene is in the range of 50 to 100%.
The selectivity of the reaction towards mononitrobenzene is 100%.

In another embodiment, the present invention further provides a grafted hydrophobic solid acid catalyst that does not get deactivated during the nitration of benzene and is recycled.

DETAILED DESCRIPTION OF THE INVENTION

The invention will now be described in detail in connection with certain preferred and optional embodiments, so that various aspects thereof may be more fully understood and appreciated.

The present invention provides a process for nitration of benzene and grafted hydrophobic solid acid catalyst for use in nitration of benzene.

In an embodiment, the present invention provides a process for nitration of benzene comprising the steps of:
a) charging benzene and a grafted hydrophobic solid acid catalyst in the range of 1:0.1 to 1:1 in a reactor flushed with nitrogen followed by refluxing the reaction mixture at temperature in the range of 90 to 110° C. for the period in the range of 1 to 2 hour and
b) adding nitric acid to the reaction mixture of step (a) with constantly removing the water formed by azeotropic distillation followed by refluxing the reaction mixture at temperature in the range of 90 to 110° C. for the period in the range of 6 to 8 hour to afford mononitrobenzene.

In a preferred embodiment, the solid acid catalyst is, $WO_3/SiO_2$ catalyst which is post grafted with commercial organosilanes.

The conversion of benzene is in the range of 50 to 100%.
The selectivity of said reaction towards mononitrobenzene is 100%.

To prevent the deactivation of the catalyst during the nitration process of benzene, the inventor discloses a process to make the catalyst of the invention hydrophobic. The grafted hydrophobic solid acid catalyst is disclosed with high activity for liquid phase nitration of benzene. The nitration of benzene has been carried out using commercial 70% nitric acid without using any solvent. The $HNO_3$ conversion obtained is 80-85% with recovery of remaining 20-15% $HNO_3$. The catalyst is recycled efficiently.

In another embodiment, the present invention provides a grafted hydrophobic solid acid catalyst that does not get deactivated during the nitration of benzene.

In a preferred embodiment, the grafted hydrophobic solid acid catalyst is $WO_3/SiO_2$ grafted with alkyl triethoxysilane.

In prior art, unmodified $WO_3/SiO_2$ catalyst is used but in preset invention to use additional solvent (ethylene dichloride) for removal of water. Without the additional solvents the reaction is not effective due to hydrophilic nature of the catalyst. Whereas in present invention when the catalyst is modified to make it more hydrophobic, no need of additional solvent for removal of water. In the present disclosure simple $HNO_3$ (65-70%) is used for nitration which is very safe for handling. This does not need high pressure autoclave for reaction. Reaction is carried out in simple glass vessel.

The $WO_3/SiO_2$ catalyst is post grafted with commercial organosilane to make it hydrophobic. The organosilane used to improve the hydrophobic nature of the catalyst is Dynasylan 9896. The ethoxy groups of alkyl triethoxysilane reacts with surface Si—OH to form covalent Si—O—Si bond upon hydrolysis.

Figure 1:
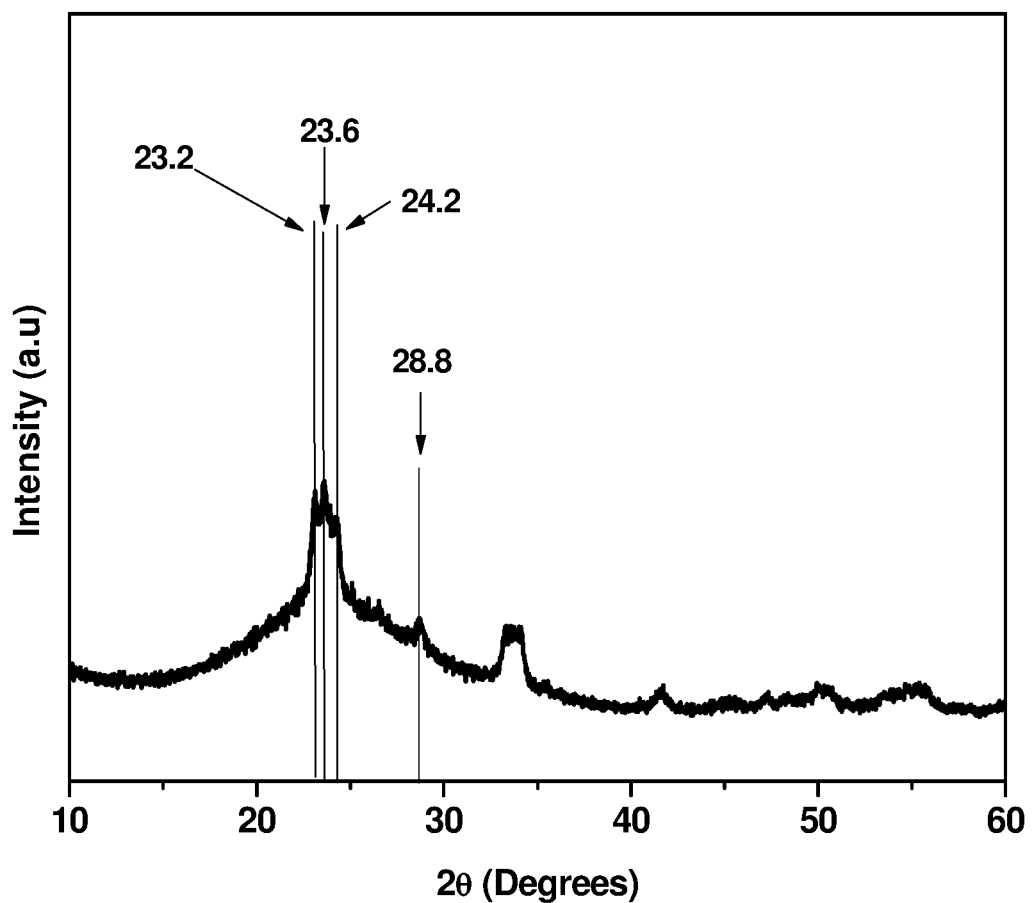
FIG. 1: XRD pattern of catalyst prepared in example 3

The powder X-ray diffraction patterns of the catalysts were recorded on PAN anlyticalX'Pert Pro Dual Goniometer diffractometerX'celerator solid state detector was employed for the experiments with $CuK\alpha$ (1.542 Å) radiation and a Ni filter (FIG. 1). The PXRD patterns of the catalyst synthesized in example 3 shown in FIG. 1. The XRD patterns exhibited sharp peaks corresponding to monoclinic $WO_3$ phase at 23.2°, 23.6°, 24.2°, 26.6°, 28.8° and 33.5° corresponding to (002), (020), (220) and (202) planes of monoclinic crystalline $WO_3$ phase (JCPDS No. 43-1035) on the broad underlying peak characteristic of the amorphous silica at $2\theta=24°$. It is observed that monoclinic phase of $WO_3$ is unaltered.

Figure 2:
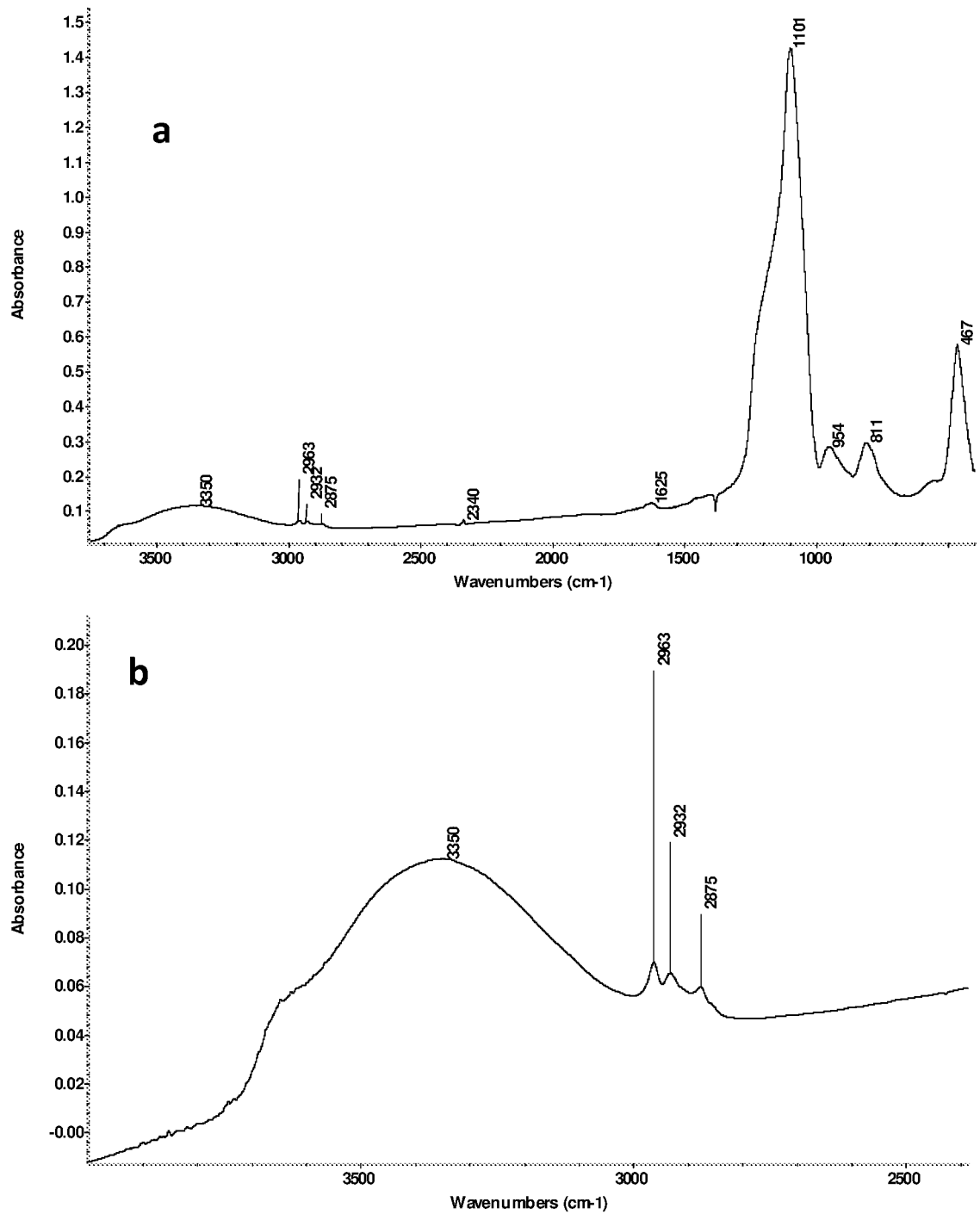
FIG. 2: FTIR spectra of catalyst prepared in example 3

The Fourier transform infrared (FT-IR) spectra of the samples are recorded on a Thermo Nicolet Nexus 670 IR instrument at ambient conditions using KBr pellets with a resolution of 4 $cm^{-1}$ in the range of 4000-400 $cm^{-1}$ averaged over 100 scans. KBR pelleted FTIR spectrum of catalyst synthesized in example 3 is presented in FIG. 2. The prominent bands around 1300-1000 $cm^{-1}$ could be assigned to the asymmetric, symmetric stretching and bending vibrations of Si—O—Si, respectively whereas the bands at 942 and 802 $cm^{-1}$ were due to the $W=O_t$ and W—O—W stretching vibrations, respectively. The IR band at 468 $cm^{-1}$ is due to O—Si—O bending vibrations. The bands in the region of 2800-3100 cm$^{-1}$ were attributed to the C—H stretching vibrations of —CH$_2$ and —CH$_3$ groups from alkyl triethoxysilane grafted on SiO$_2$.

Figure 3:
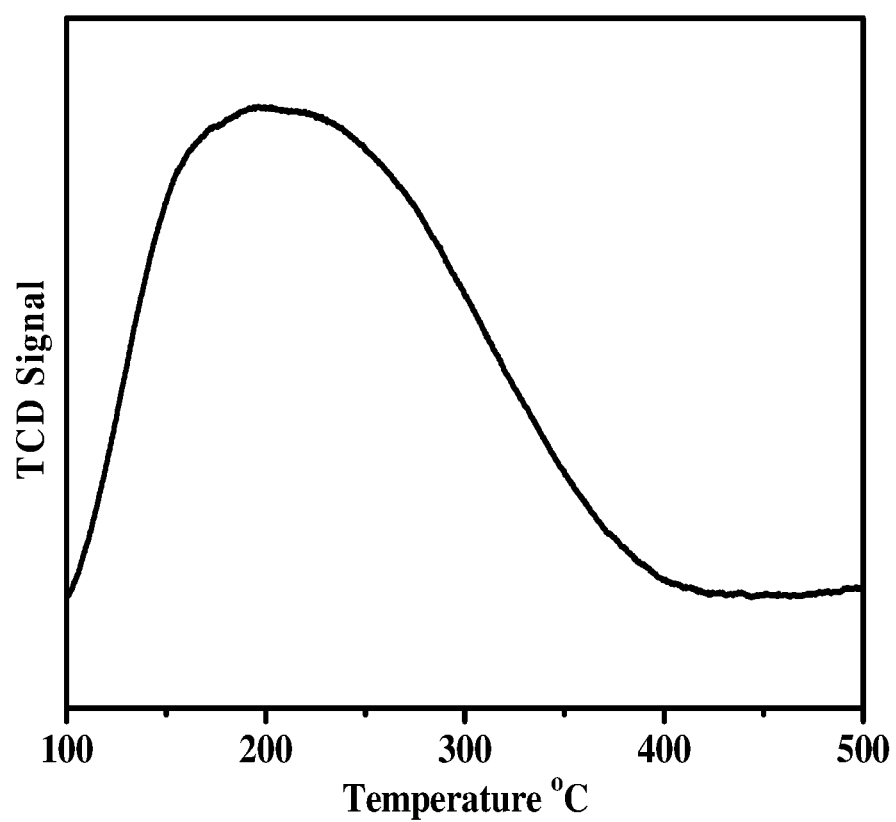
FIG. 3: $NH_3$-TPD of catalyst prepared in example 3

The ammonia-TPD experiments are carried out to determine the acid strength of the catalyst synthesized in example 3 is shown in FIG. 3. The ammonia desorption curve of example 3 indicated presence of maximum number of medium and weak acid sites (150-350° C.) with total acidity of 0.54 mmol/g.

Figure 4:
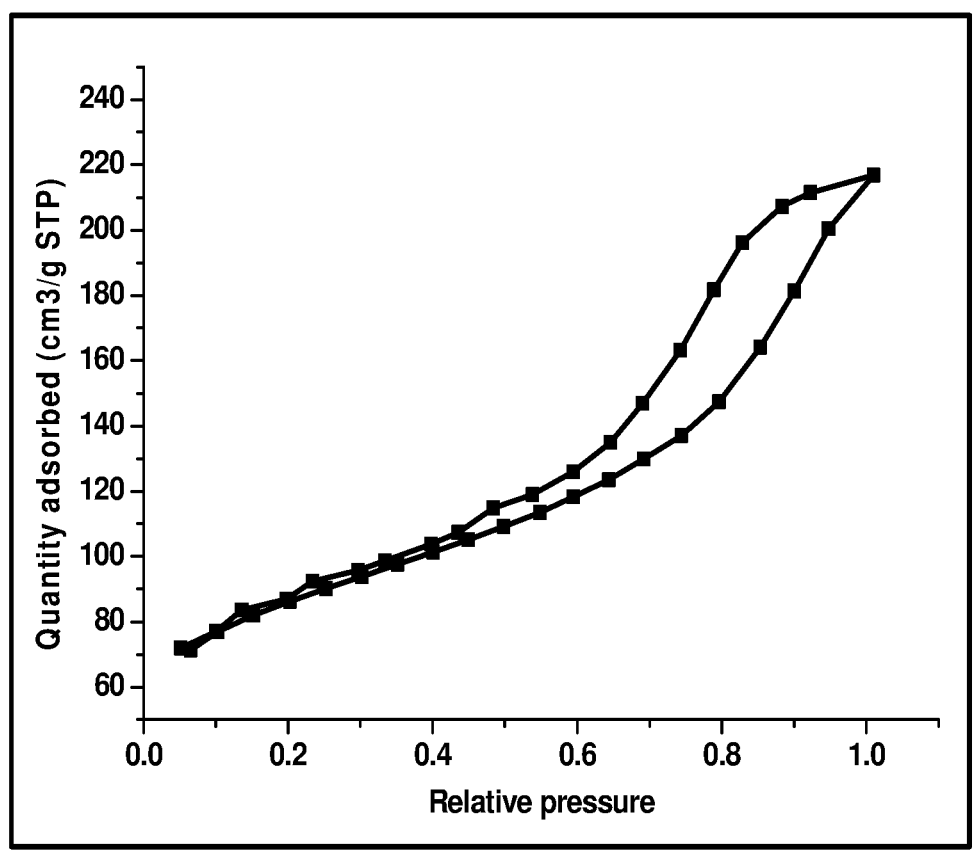
FIG. 4: BET surface analysis of catalyst prepared in example 3
Figure 5:
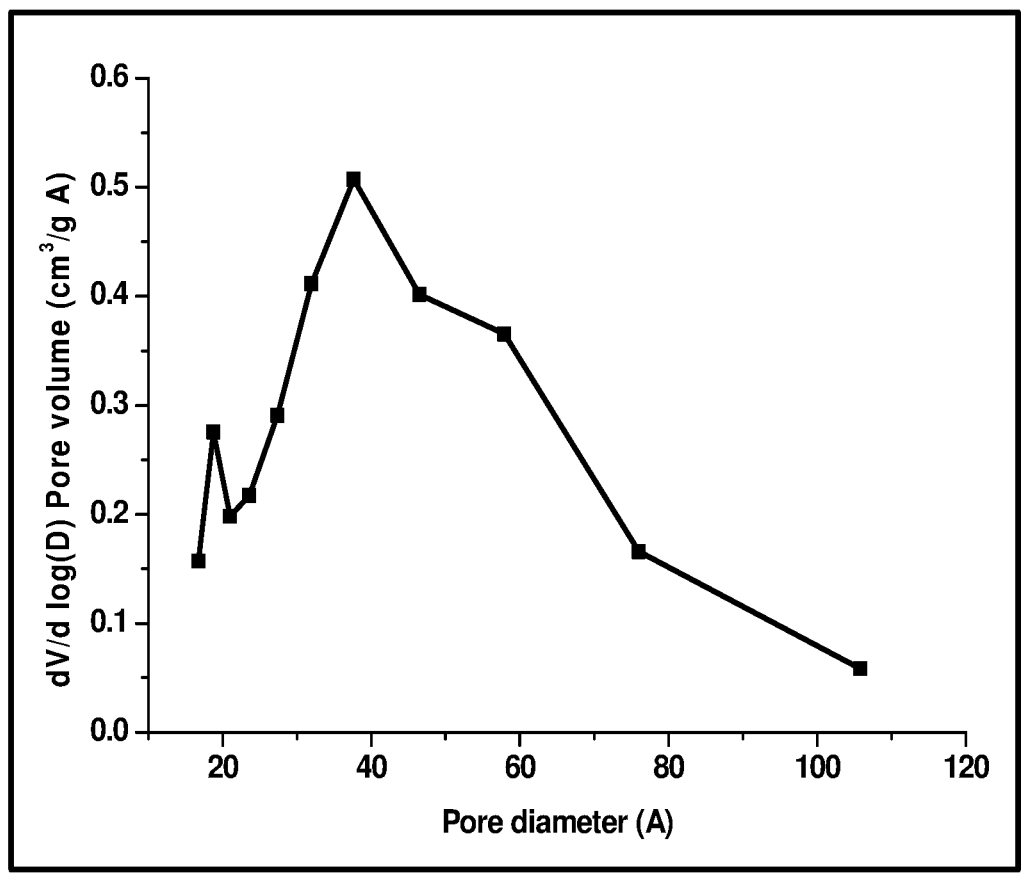
FIG. 5: Pore size distribution of catalyst prepared in example 3

The surface analysis of catalyst synthesized in example 3 was carried out using BET method and results are shown in Table 1. A very high surface area of 302 m$^2$/g was observed for example 3 because of sol-gel technique using ES-40 as the silica source. The total pore volume is 0.33 cc/g, with pore size 20.5 Å (FIG. 4).

EXAMPLES

Following examples are given by way of illustration therefore should not be construed to limit the scope of the invention.

Example 1: Catalyst Preparation

In a 50 mL beaker, 4.25 g ammonium metatungstate was dissolved in 10 mL distilled water. In another 250 mL beaker, a solution of 40 g ethyl silicate-40 and 30 g isopropyl alcohol was stirred for 1 h and to this solution aqueous solution of ammonium metatungstate was added drop wise. This solution was stirred for 3 h followed by addition of 2 mL 2.5% aqueous ammonia solution. The solution was stirred until a white colored gel was obtained. This gel was air dried and calcined at 500° C. for 5 h to obtain 20% WO$_3$/SiO$_2$ catalyst.

Example 2: Synthesis of Modified Catalyst

In a typical procedure, 5.0 g 20% WO$_3$/SiO$_2$ catalyst as prepared in Example 1, was dispersed in 25 mL dry toluene. To this solution 0.08 g of alkyl triethoxysilane (Dynasylan 9896) was added and the resultant mixture was heated at 80° C. with constant mixing on rotary evaporator for 8 h. Then toluene was evaporated under vacuum and resultant powder was dried in oven at 100° C. for 5 hrs.

Example 3: Synthesis of Modified Catalyst

In a typical procedure, 5.0 g 20% WO$_3$/SiO$_2$ catalyst as prepared in Example 1, was dispersed in 100 mL dry toluene. To this solution 0.265 g of alkyl triethoxysilane (Dynasylan 9896) was added and the resultant mixture was heated at 80° C. with constant mixing on rotary evaporator for 8 h. Then toluene was evaporated under vacuum and resultant powder was dried in oven at 100° C. for 5 hrs.

Example 4: Synthesis of Modified Catalyst

In a typical procedure, 5.0 g 20% WO$_3$/SiO$_2$ catalyst as prepared in Example 1, was dispersed in 100 mL dry toluene. To this solution 0.4 g of alkyl triethoxysilane (Dynasylan 9896) was added and the resultant mixture was heated at 80° C. with constant mixing on rotary evaporator for 8 h. Then toluene was evaporated under vacuum and resultant powder was dried in oven at 100° C. for 5 hrs.

Example 5: BET Surface Analysis

The BET surface area of the calcined samples was determined by N$_2$ sorption at −196° C. using NOVA 1200 (Quanta Chrome) equipment. Prior to N$_2$ adsorption, the materials were evacuated at 300° C. under vacuum. The specific surface area, BET, was determined according to the BET equation.

TABLE 1

| Surface analysis and acidity of the catalysts | | | | |
|---|---|---|---|---|
| Sample | Surface area m$^2$/g | Pore volume cc/g | Pore radius Å | NH$_3$ desorbed mmol/g |
| Catalyst as in Example 3 | 302 | 0.33 | 20.5 | 0.54 |

Example 6: NH$_3$-TPD Experiment

The NH$_3$-TPD experiments were performed using a Micromeritics Autochem 2910 instrument. A weighed amount of the sample (~100 mg) was placed in a quartz reactor, pretreated in a flow of helium gas at 500° C. for 1 h (ramp rate of 10° C.min$^{-1}$) and cooled to 100° C. The catalyst was then exposed to NH$_3$ gas (5% NH$_3$-95% He, 50 mLmin$^{-1}$) at 100° C., followed by evacuation at 100° C. for 3 h. Then, the desorbed NH$_3$ was measured from 100° C. to 700° C. with a heating rate of 5° C.min$^{-1}$ in flow of helium as a carrier gas at a flow rate of 60 mLmin$^{-1}$ until ammonia was desorbed completely. Ammonia-TPD experiments were carried out to determine the acid strength of the catalyst synthesized in example 3 is shown in FIG. 3. The ammonia desorption curve of example 3 indicated presence of maximum number of medium and weak acid sites (150-350° C.) with total acidity of 0.54 mmol/g.

Example 7: Nitration of Benzene

A 250 mL three-necked round bottom flask fitted with Dean-Stark apparatus was charged with 100 g benzene and 10 g catalyst as prepared in example 2. The flask was flushed with nitrogen. The solution was refluxed at 90° C. for 1 h. Then 61.7 mL of 70% HNO$_3$ was added to the reaction flask dropwise. The water formed during the reaction was removed azeotropically using the Dean-Stark apparatus. The reaction was carried out for 8 h. The reaction was monitored by GC analysis. In this reaction 50% conversion of benzene was obtained with 100% selectivity for mononitrobenzene.

Example 8: Nitration of Benzene

A 250 mL three-necked round bottom flask fitted with Dean-Stark apparatus was charged with 100 g benzene and 10 g catalyst as prepared in example 3. The flask was flushed with nitrogen. The solution was refluxed at 90° C. for 1 h. Then 61.7 mL of 70% HNO$_3$ was added to the reaction flask dropwise. The water formed during the reaction was removed azeotropically using the Dean-Stark apparatus. The reaction was carried out for 8 h. The reaction was monitored by GC analysis. In this reaction 60% conversion of benzene was obtained with 100% selectivity for mononitrobenzene.

Example 9: Nitration of Benzene

A 250 mL three-necked round bottom flask fitted with Dean-Stark apparatus was charged with 100 g benzene (1.28 mol) and 10 g catalyst as prepared in example 4. The flask was flushed with nitrogen. The solution was refluxed at 90°

C. for 1 h. Then 61.7 mL of 70% HNO₃ was added to the reaction flask dropwise. The water formed during the reaction was removed azeotropically using the Dean-Stark apparatus. The reaction was carried out for 8 h. The reaction was monitored by GC analysis. In this reaction 46% conversion of benzene was obtained with 100% selectivity for mononitrobenzene.

Example 10: Nitration of Benzene

A 250 mL three-necked round bottom flask fitted with Dean-Stark apparatus was charged with 100 g benzene and 10 g catalyst as prepared in example 3. The flask was flushed with nitrogen. The solution was refluxed at 90° C. for 1 h. Then 93.1 mL of 50% HNO₃ was added to the reaction flask dropwise. The water formed during the reaction was removed azeotropically using the Dean-Stark apparatus. The reaction was carried out for 8 h. The reaction was monitored by GC analysis. In this reaction 30% conversion of benzene was obtained with 100% selectivity for mononitrobenzene.

Example 11: Nitration of Benzene

A 250 mL three-necked round bottom flask fitted with Dean-Stark apparatus was charged with 62.4 g benzene and 2.88 g catalyst as prepared in example 3. The flask was flushed with nitrogen. The solution was refluxed at 90° C. for 1 h. Then 7.6 mL of 90% HNO₃ was added to the reaction flask dropwise. The water formed during the reaction was removed azeotropically using the Dean-Stark apparatus. The reaction was carried out for 8 h. The reaction was monitored by GC analysis. In this reaction 40% conversion of benzene was obtained with 100% selectivity for nitrobenzene.

Example 12: Nitration of Benzene

A 250 mL three-necked round bottom flask fitted with Dean-Stark apparatus was charged with 100 g benzene and 10 g catalyst as prepared in example 2. The flask was flushed with nitrogen. The solution was refluxed at 110° C. for 1 h. Then 61.7 mL of 70% HNO₃ was added to the reaction flask dropwise. The water formed during the reaction was removed azeotropically using the Dean-Stark apparatus. The reaction was carried out for 8 h at 110° C. The reaction was monitored by GC analysis. In this reaction 45% conversion of benzene was obtained with 100% selectivity for mononitrobenzene.

Example 13: Catalyst Recycle Study

A 250 mL three-necked round bottom flask fitted with Dean-Stark apparatus was charged with 100 g benzene and 10 g catalyst as prepared in example 3. The flask was flushed with nitrogen. The solution was refluxed at 90° C. for 1 h. Then 61.7 mL of 70% HNO₃ was added to the reaction flask dropwise. The water formed during the reaction was removed azeotropically using the Dean-Stark apparatus. The reaction was carried out for 8 h. The reaction was monitored by GC analysis. In this reaction 60% conversion of benzene was obtained with 100% selectivity for mononitrobenzene. After completion of reaction the reaction mixture was decanted leaving behind the catalyst in the flask and to the same flask fresh charge was added. Similarly such 4 recycles were carried out and the conversion and selectivity in each cycle is given below:

TABLE 2

Catalyst Recycle study

| Sr. No. | Recycle no. | Benzene Conversion, % | Nitrobenzene selectivity % |
|---|---|---|---|
| 1 | 0 | 60 | 100 |
| 2 | 1 | 60 | 100 |
| 3 | 2 | 58 | 100 |
| 4 | 3 | 61 | 100 |
| 5 | 4 | 59 | 100 |

Advantages of the Invention

1) No use of sulphuric acid and hence no formation of byproduct waste. Environmentally benign process.
2) No use of conc. sulphuric acid and fuming nitric acid, hence no use of costly material of construction for the process plant.
3) A new composition of hydrophobic WO₃/SiO₂ quite active and selective for liquid phase nitration of benzene.
4) Catalyst successfully recycled up to 4 cycles without losing its activity.
5) Commercial nitric acid of 65-70% concentration can be used for nitration reaction, hence less handling hazards as well as lower cost.

We claim:

1. A benzene nitration catalyst comprising hydrophobic solid acid WO₃/SiO₂ grafted with an organosilane selected from a C2 to C10 alkyl trialkoxysilane.

2. The benzene nitration catalyst of claim 1, wherein the alkoxy in the C2 to C10 alkyl trialkoxysilane is methoxy, ethoxy or propoxy.

3. A process for preparing a benzene nitration catalyst comprising the steps of:
   a. dispersing 20% WO₃/SiO₂ in dry toluene to form a mixture:
   b. adding an organosilane selected from an alkyl trialkoxysilane to the mixture of step a;
   c. heating the resultant mixture of step b with constant mixing to obtain a powder and
   d. drying the resultant powder of step c to obtain the benzene nitration catalyst.

4. The process of claim 3, wherein the a ratio of WO₃/SiO₂ to the dry toluene is 1:4 to 1:20.

5. The process of claim 3, wherein the benzene nitration catalyst is-comprises solid WO₃/SiO₂ grafted with the organosilanes.

6. The process of claim 3, wherein in step d, the resultant powder of step c is dried in an oven.

7. A process for nitration of benzene comprising the steps of:
   a) charging benzene and a grafted hydrophobic solid acid catalyst in the range of 1:0.1 to 1:1 in a reactor flushed with nitrogen to form a reaction mixture followed by refluxing the reaction mixture at a temperature in the range of 90 to 110° C. for a period in the range of 1 to 2 hour and
   b) adding nitric acid to the reaction mixture of step (a) with constantly removing by azeotropic distillation of the water formed followed by refluxing the resultant reaction mixture at a temperature in the range of 90 to 110° C. for a period in the range of 6 to 8 hour to form a mononitrobenzene.

8. The process of claim 7, wherein the hydrophobic solid acid catalyst is WO₃/SiO₂.

9. The process of claim 7, wherein conversion of the benzene to the mononitrobenzene is in the range of 50 to 100%.

10. The process of claim 7, wherein selectivity of forming the mononitrobenzene is 100%.

11. The process of claim 7, wherein the grafted hydrophobic solid acid catalyst does not get deactivated during the nitration of benzene and is recycled.

12. The process of claim 7, wherein the grafted hydrophobic solid acid catalyst comprises hydrophobic solid acid $WO_3/SiO_2$ grafted with an organosilane.

* * * * *